United States Patent [19]

Cushman et al.

[11] 4,216,383

[45] Aug. 5, 1980

[54] EXPEDITIOUS UNI-DIRECTIONAL PANORAMIC DENTAL RADIOGRAPHY

[75] Inventors: Robert H. Cushman, Princeton; Fred W. Hart, Jr., Barnegat, both of N.J.; David R. Kircher; Anthony Ciavattoni, both of Staten Island, N.Y.

[73] Assignee: Pennwalt Corporation, Philadelphia, Pa.

[21] Appl. No.: 947,366

[22] Filed: Oct. 2, 1978

[51] Int. Cl.² ............................................ G03B 41/16
[52] U.S. Cl. ............................................... 250/439 P
[58] Field of Search ..................... 250/445 R, 439 P

[56] References Cited

U.S. PATENT DOCUMENTS 4,125,774 11/1978 Ciavattoni et al. .............. 250/445 R Primary Examiner—Alfred E. Smith
Assistant Examiner—T. N. Grigsby

[57] ABSTRACT

Handling rate of patients being processed for panoramic dental radiographing when tubehead-camera assembly of a low silhouette panoramic dental X-ray machine is rotated for a scan in one direction only is substantially equalized with the conventional bi-directional scan, thus minimizing disadvantages concomitant with the latter. Structure is described which effects fast return of the tubehead-camera assembly with its simultaneous elevation for facilitating the radiographed patient's exit from the machine and the entrance of another patient.

3 Claims, 6 Drawing Figures

EXPEDITIOUS UNI-DIRECTIONAL PANORAMIC DENTAL RADIOGRAPHY

STATEMENT OF THE INVENTION

This invention relates to improved methods for expediting patient handling rate when employing low silhouette panoramic dental X-ray apparatus.

CROSS-REFERENCE TO RELATED APPLICATIONS

Reference is hereby made to copending patent application Ser. No. 856,423, filed Dec. 1, 1977, now U.S. Pat. No. 4,168,633 for "Excursion Mechanism for Panoramic Dental X-Ray Machine" of Anthony Ciavattoni et al., assigned to the present assignee.

BACKGROUND AND SUMMARY OF INVENTION

A typical low silhouette panoramic dental X-ray machine is characterized by a vertical column which is supported by and rotatably mounted to a base structure, the column carrying, at its upper portion, the tubehead and camera assembly which rotates as a unit with the column about the patient's head. A rigid curved arm interconnects the tubehead and camera while maintaining a space therebetween for positioning of the patient's head. The tubehead and camera orbit the patient's head for a limited number of degrees of rotation in order to accomplish the panoramic radiographing or scan of the dental arch structure which scan consumes about 22 seconds. After the scan, the patient cannot readily exit the machine because of the presence of the rigid arm immediately to the fore. Thus, the column must be returned to its original starting position which also consumes about 22 seconds. The camera however yet blocks the convenient exit of the patient and thus the tubehead-camera assembly must be elevated, consuming approximately 11 more seconds for about 11 inches of travel. Thus, the total period of time consumed in radiographing one patient comprised a minimum of about 55 seconds.

It is significant to realize that even if the machine were designed to take radiographs in both rotational directions, which characterizes most current panoramic machines, a minimum of 33 seconds would be required for each patient, i.e., 22 seconds for the panoramic scan; and 11 seconds for the elevation of the tubehead-camera assembly to facilitate the patient's exit, as well as the entrance of the waiting patient.

Where radiographs are taken in both directions of rotation however, a significant tendency for unwanted variations in the radiographs frequently occur due to imperfect leveling of the machine. Other variations as well as non-reproducible radiographs result from a lack of synchronization among the different motors controlling film drive, chair shift, and camera position, when these motors are operated in both directions. These deficiencies are particularly important in the continuous mode of panoramically radiographing the centrals region where a very critical relationship exists among such variables.

Thus, it is preferable to radiograph in one direction of rotation only. However, in busy hospital clinics, Army hospitals, and the like, where patients are oftentimes waiting to be radiographed, and clinicians are anxious to cooperate, it is most desirable if the patient handling rate could be improved.

The present invention provides improved processes, and structures in support thereof, for expediting patient handling rate when panoramically radiographing dental patients in one direction only by means of low silhouette, or low center of gravity X-ray apparatus.

To more fully understand and appreciate the significance of the invention, reference is made to U.S. Pat. Nos. 2,798,958; 3,045,118; and 3,636,349, which disclose various types of structures, apparatus and mechanisms for orbiting tubehead-camera assemblies in circular or arcuate paths; for varying film travel speed in accordance with tubehead-camera assembly movements; for shifting the patient in a chair; and for providing continuous or discontinuous type radiographic images.

DETAILED DESCRIPTION OF THE INVENTION

Figures 1, 5:
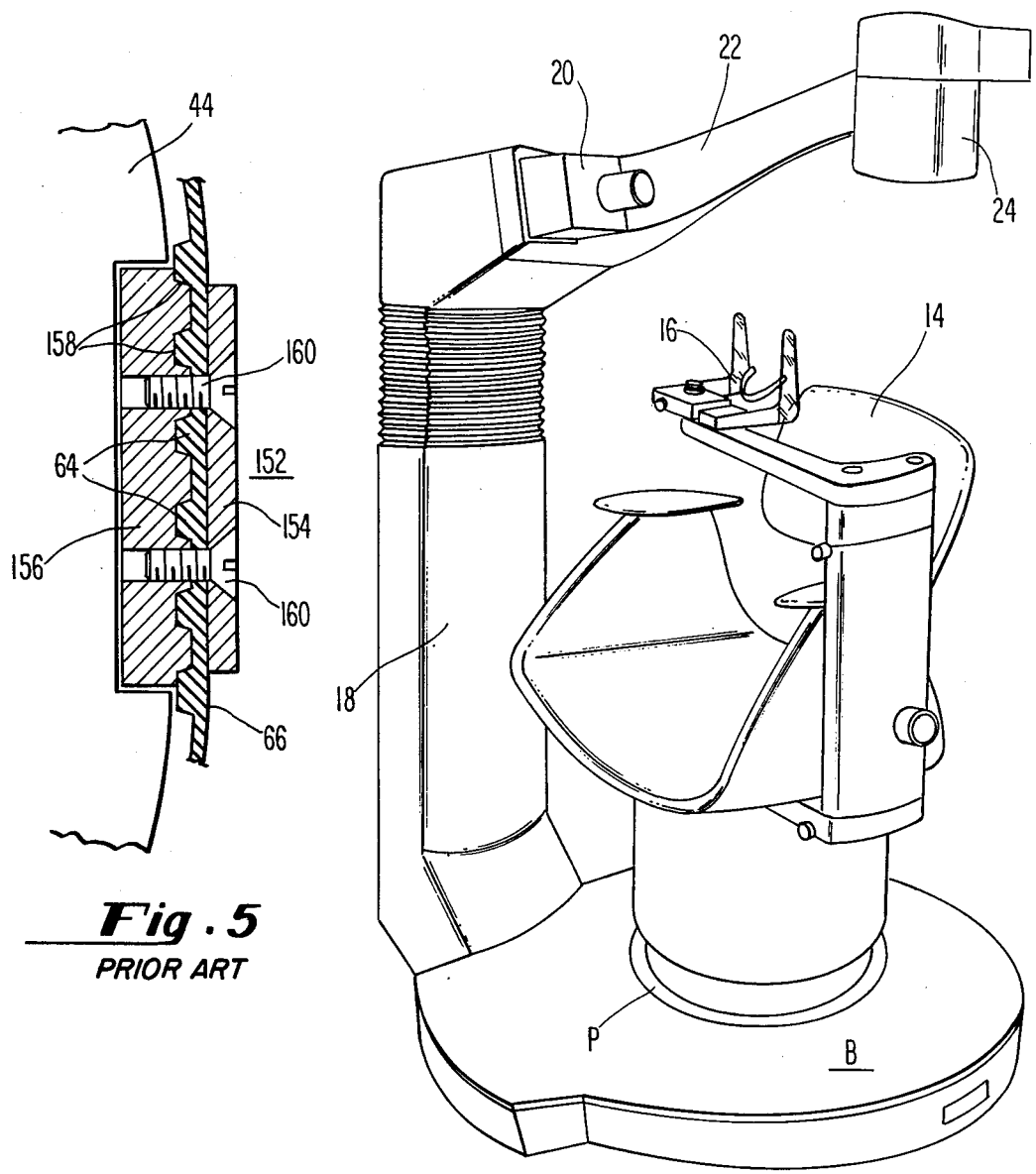
FIG. 1 is a perspective view of typical prior art dental X-ray apparatus of the present assignee.
FIG. 5 is a sectional view of the belt-fastening means used in the excursion mechanism.

Referring to FIG. 1 of the drawings, the panoramic X-ray apparatus comprises a base B which supports and partially houses the excursion mechanism. A stationary platform P is disposed generally centrally of the base B, the platform carrying a patient chair 14 including means 16 for supporting the chin and head of a patient. A column 18 is caused to rotate around chair 14 by means of the excursion mechanism. Column 18 includes a tubehead 20, a camera supporting arm 22 and a camera 24 which includes the usual film holding means. Tubehead 20, camera 24 and camera supporting arm 22 comprise a tubehead-camera assembly. Conventional motor and screw means for elevating or lowering the tubehead-camera assembly is contained within column 18.

Figure 2:
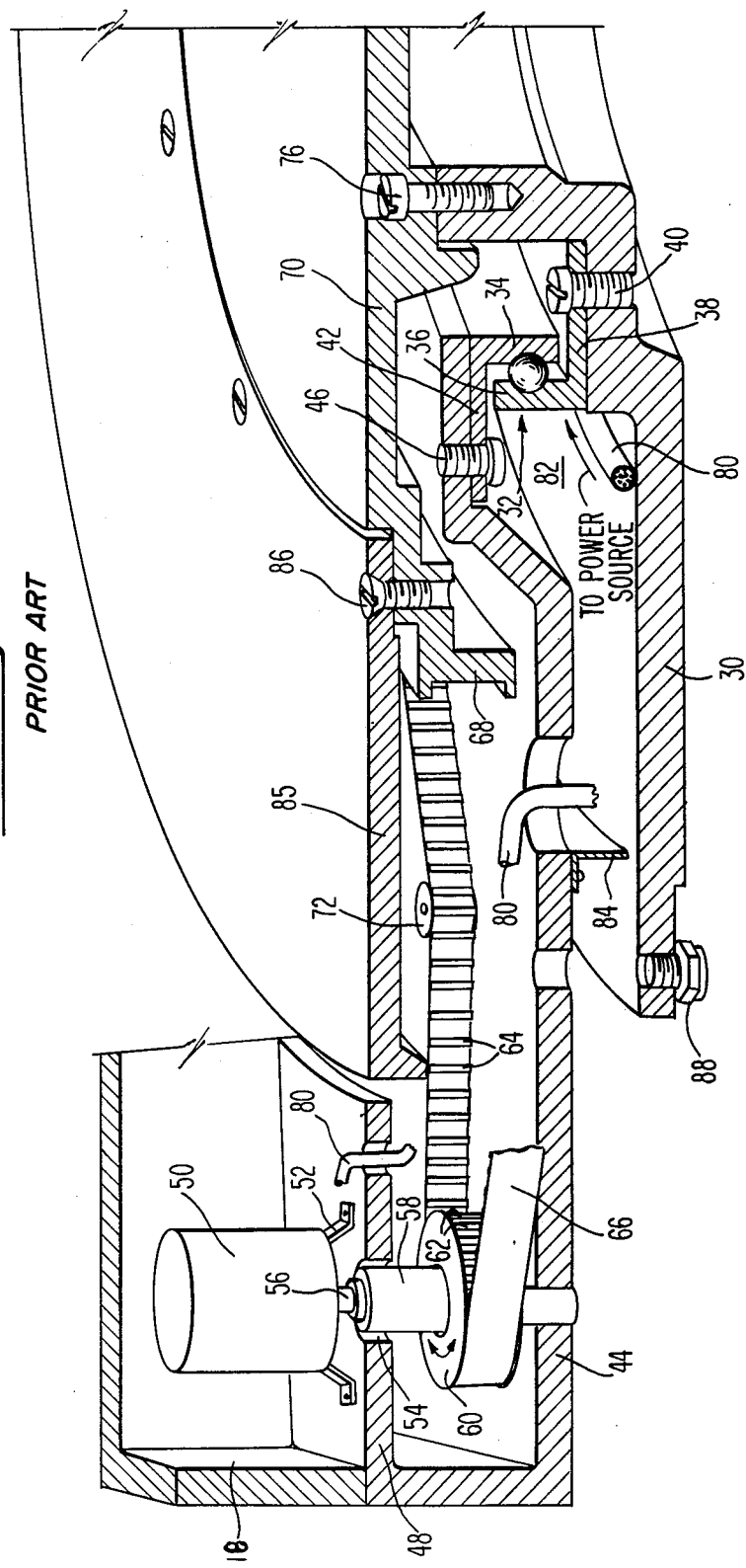
FIG. 2 is a cutaway perspective view of a portion of the base and excursion mechanism of the embodiment shown in FIG. 1.

In FIG. 2, a base plate 30, preferably an aluminum casting, carries a circular flange mounted bearing 32 having an inner race 34 and an outer race 36. Outer race 36 includes a lower flange 38 which is secured to base plate 30 by circumferentially spaced screws 40. Similarly, upper flange 42 of inner race 34 carries rotating disc 44. Upper flange 42 and rotating disc 44 rotate as a unit and are held together by means of circumferentially spaced shoulder screws 46.

Rotating disc 44 carries column 18 which is provided with a horizontal plate member 48, upon which is mounted a synchronous motor 50 by means of brackets 52. Motor 50 is conveniently 2-speed with a fast reverse, or motor 50 may be provided with additional clutches, and/or gears other convenient means for doubling its speed in the other direction. An opening 54 is provided in horizontal plate 48 through which shaft 56 of motor 50 communicates with conventional electromagnetic slip clutch 58. Clutch 58 serves to couple shaft 56 with sprocket 60 which is rotatably mounted to rotating disc 44. Sprocket 60 is provided with teeth 62 which coact with spaced projections 64 on a belt 66. The belt is accommodated within an annulus 68 provided around stationary platform 70 which supports the patient chair 14.

It should be emphasized that belt 66 does not rotate around platform 70. Belt 66 is held immovable against annulus 68 at that portion of the annulus farthest removed from sprocket 60 by means to be described more fully hereinafter. To further clarify, any given point on belt 66, such as point E (FIG. 4) for example, will always contact a specified point, and no other point, on annulus 68 provided around platform 70, such as point F, regardless of the direction of rotation of rotating disc 44. Belt 66 provides the means therefore for translating the rotation of sprocket 60 into orbital rotation of rotating disc 44 and column 18.

A fixed idler pulley 72 is rotatably mounted to rotating disc 44, while an adjustable idler pulley assembly 74 (FIG. 4) is pivotally mounted to rotating disc 44, both pulleys cooperating to maintain proper tension of belt 66 against sprocket 60 and annulus 68. Platform 70 is fixedly secured to base plate 30 by screws 76.

A flexible electric cable 80 passes up through column 18 for connecting the power source to the X-ray source and camera, and to the motor (not shown) which elevates or lowers the tubehead assembly on column 18. The cable is also connected to motor 50, slip clutch 58, and a limit switch assembly to be later described. In order to insure unimpeded vertical movement of the tubehead assembly and the orbiting of column 18, cable 80 will be provided with a sufficient length. To that end, a space 82 is provided above base plate 30 to permit coiling and uncoiling of cable 80 during movement of the tubehead assembly and column. A cable control band 84 is mounted to an underside portion of rotating disc 44 for restricting cable 80 within space 82.

A removable cover plate or step plate 85, suitable an aluminum casting, protects the excursion mechanism as well as affording means upon which the patient may step and rest his feet. Step plate 85 is removably attached to stationary platform 70 by screws 86. Leveling screws 88 are provided in base plate 30.

Figure 3:
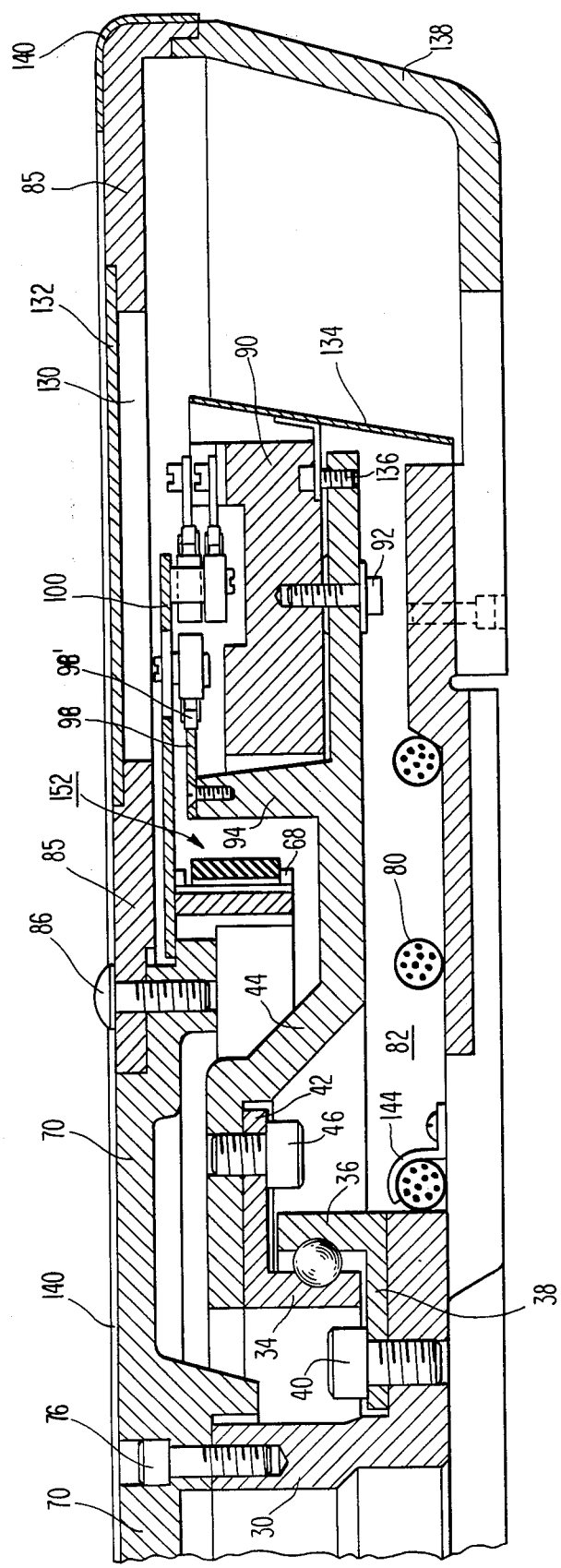
FIG. 3 is a sectional view of another portion of the base and excursion mechanism.
Figure 4:
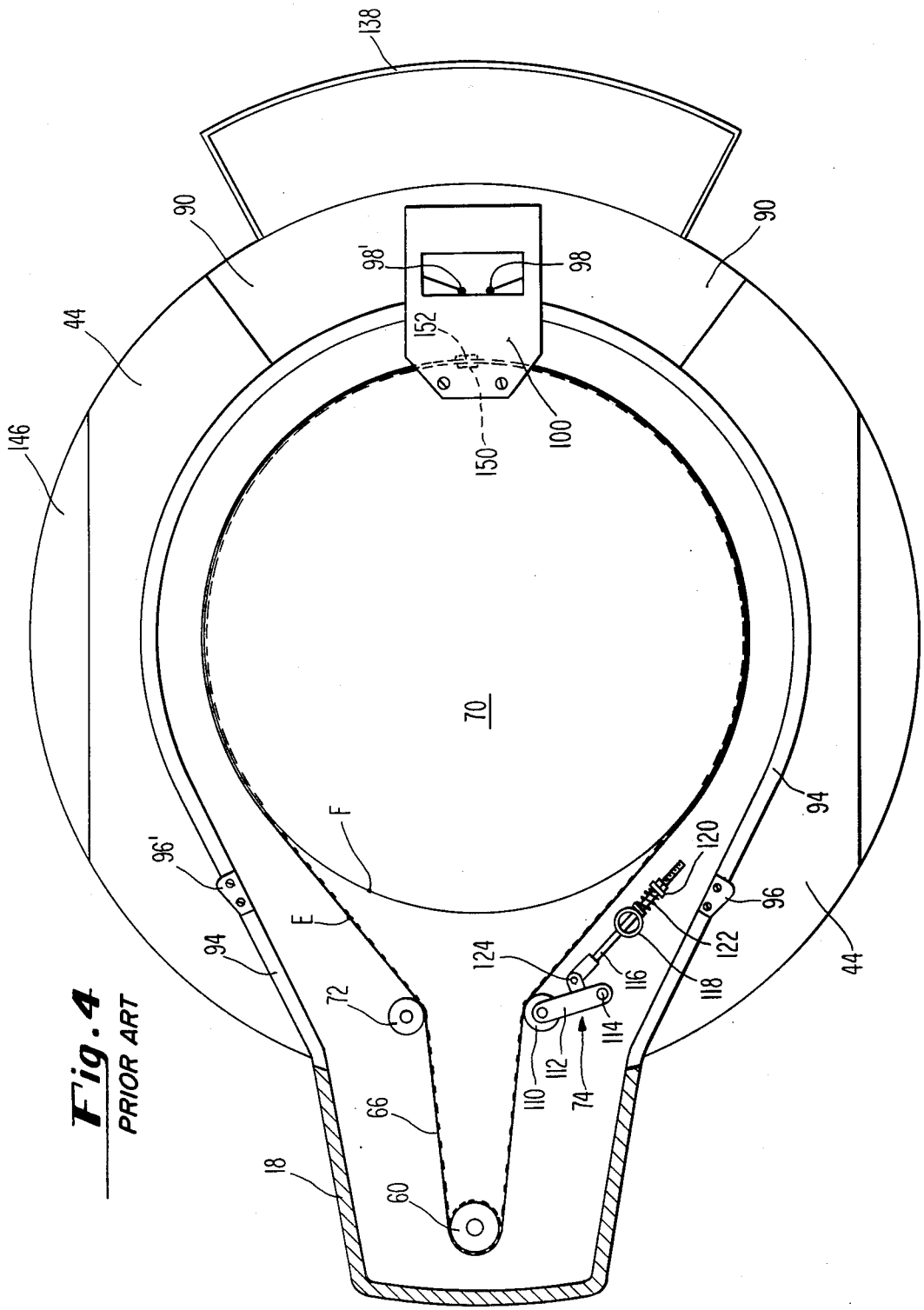
FIG. 4 is a plan view, partially in section, of the excursion mechanism with portions removed for clarity.

For a better understanding of the mechanism, reference should now be made to FIGS. 3 and 4 wherein a balancing weight 90, suitably cast iron, is shown seated on an outer portion of rotating disc 44, the weight 90 being positioned in counterbalancing relation to column 18. Screws 92 maintain balance weight 90 in a fixed position on rotating disc 44. An annular ring 94 upstands from rotating disc 44 and carries a pair of cams 96 and 96' which respectively actuate limit switches 98 and 98' to limit the total excursion of rotating disc 44 to about 240° in either direction and to automatically return rotating disc 44, in a counterclockwise direction after the patient has been radiographed in the clockwise direction. Motor 50 however, will return rotating disc 44 in the counterclockwise direction at double the speed, or in one-half the time, which rotating disc 44 travels in the clockwise or radiographing direction. Limit switches 98 and 98' are carried on a switch plate 100 mounted on stationary platform 70. More specifically, when rotating disc 44 moves in a clockwise direction, switch 98' will be actuated by cam 96' to close the circuit to the fast reverse of motor 50 and to the elevating motor to thereby effect a fast return of rotating disc 44, and hence the tubehead-camera assembly while elevating the latter simultaneously therewith. Rotating disc 44 ceases its counterclockwise return when limit switch 98 is actuated by cam 96. Upper limit of elevation of the tubehead-camera assembly is controlled by conventional limit switch arrangement. Circuitry for the cams-limit switches-motors is conventional and is not detailed herein.

Adjustable idler pulley assembly 74 comprises an idler wheel 110 rotatable on arm 112 which is pivotally mounted to rotating disc 44 by screw 114. A holder 116 is slidably insertable through a nut 118 which is fixedly secured to rotating disc 44. Thus, idler wheel 110 will be displaced inwardly to increase tension on belt 66 when screw 120 is tightened against compression spring 122 to cause arm 112 to pivot clockwise on screw 114 by means of pivot pin 124.

Step plate 85 is provided with a recess 130 for receiving a removable access plate 132 for easy access to switch plate 100.

A skirt 134 extends around rotating disc 44, and is mounted thereto by screws 136 while a step plate support member 138 is bolted to base plate 30. A step plate cover 140, preferably rubber or vinyl, is fitted over the step plate.

A clamp 144 may be employed to secure cable 80 against base plate 30.

Rotating disc 44 may be provided with removable wings 146 to enable passage of the X-ray machine through restricted openings.

Annulus 68 of stationary platform 70 has a cut-out area, or notched recess 150 for receiving a belt-fastening assembly 152 therewithin (FIG. 5) comprising an outer plate 154 and an inner plate 156 which includes grooves 158 for accepting projections 64 of belt 66. The plates 154 and 156 are secured together by screws 160.

In the operation of the excursion mechanism, any rotary motion of shaft 56 of motor 50 will not be coupled to sprocket 60 until sufficient voltage is supplied to the coils of clutch 58. That is, the clutch will be permitted to "slip" until actuated. However, once actuated by a sufficient voltage, rotation of sprocket 60 will be effected. Since belt 66 is held fast against annulus 68 in the vicinity where belt-fastening assembly 152 engages notched recess 150 provided in stationary platform 70, rotation of the sprocket causes column 18 and rotating disc 44 to orbit around the stationary patient platform. Thus, belt 66 will translate the rotational movement of sprocket 60 into a clockwise or counterclockwise excursion of the column depending upon the direction of rotation of the sprocket. More specifically, rotation of sprocket 60 in a counterclockwise direction causes rotating disc 44, column 18 and the tubehead-camera assembly to orbit in an opposite direction, and vice-versa.

Figure 6:
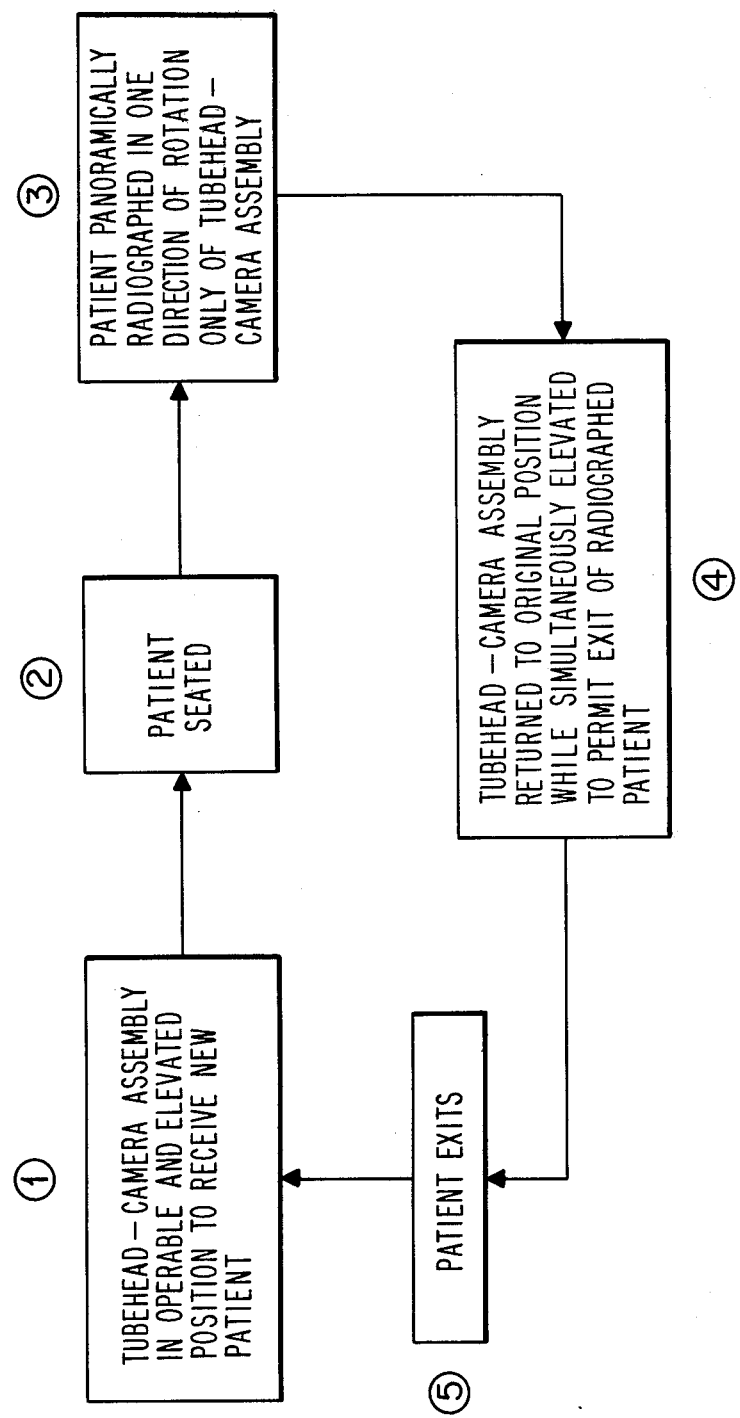
FIG. 6 is a flow diagram illustrating the uni-directional method of panoramic radiography of the present invention.

Circuitry for supplying the necessary voltage to actuate slip clutch 58 is well known. For the purposes of this invention, motor 50 is geared down to permit 1.83 rpm of the tubehead-camera assembly in the clockwise or forward direction and 3.66 rpm in the counterclockwise or return direction. The forward direction of travel consumes about 22 seconds. The return of the tubehead-camera assembly requires about 11 seconds including its simultaneous elevation. Thus, a total of about 33 seconds patient time is required, which is substantially equivalent to the time consumed in radiographing a patient on a machine which radiographs in both or alternating directions of rotation, i.e., 22 seconds for the panoramic scan and 11 seconds for raising the tubehead-camera assembly. It is understood, of course, that the radiographing direction may be accomplished in the counterclockwise direction, in which case the fast return will be in the clockwise direction. It is also understood that the return excursion and simultaneous elevation of the tubehead-camera assembly are automatically terminated for safety reasons at any time the dead-man exposure switch is released. The method of panoramically radiographing in one direction of rotation only is clearly shown in FIG. 6.

We claim:

1. In a rapid and improved method for radiographing dental patients in one direction of rotation only of a tubehead-camera assembly associated with low silhouette panoramic dental X-ray machine which method enhances the expeditious handling rate of said patients being processed for said one-direction panoramic dental radiographing, said process comprising operably positioning said patient in a chair associated with said machine, panoramically radiographing dental arch area of said positioned patient by orbiting in one direction of rotation said tubehead-camera assembly about head of said patient, automatically returning said tubehead-camera assembly after said orbit in an opposite direction of rotation while simultaneously elevating said tubehead-camera assembly comprising a total patient time substantially equivalent to patient time in taking a radiograph on a substantially equivalent machine taking successive radiographs in alternate directions of rotation of tubehead-camera assembly.

2. The process of claim 1 wherein said total patient time and said patient time each comprises about 33 seconds.

3. The process of claim 1 wherein time consumed in radiographing each patient with said substantially equivalent machine in same direction of rotation comprises at least 55 seconds.

* * * * *